United States Patent [19]

Wilson

[11] 4,354,834
[45] Oct. 19, 1982

[54] MODULAR ORTHODONTIC APPLIANCES
[76] Inventor: William L. Wilson, 15 Dix St., Winchester, Mass. 01890
[21] Appl. No.: 879,436
[22] Filed: Feb. 21, 1978
[51] Int. Cl.³ .............................................. A61C 7/00
[52] U.S. Cl. .................................... 433/21; 433/11
[58] Field of Search ............... 32/14 A, 14 C, 14 R, 32/14 E; 140/106, 123.5; 433/11, 18–22

[56] References Cited
U.S. PATENT DOCUMENTS

| | | | |
|---|---|---|---|
| 1,137,298 | 2/1913 | Walker | 32/14 E |
| 1,142,467 | 12/1915 | Walker | 32/14 E |
| 1,217,374 | 2/1917 | Walker | 32/14 A |
| 3,762,050 | 10/1973 | Dal Pont | 32/14 A |

Primary Examiner—Robert Peshock
Assistant Examiner—Michael J. Foycik, Jr.
Attorney, Agent, or Firm—Sheridan, Ross & McIntosh

[57] ABSTRACT

A modular orthodontics appliance in the form of either an arch wire or a sectional is provided which makes it possible to provide the whole spectrum of three dimensional appliance functions which are geometrically predictable, have positive directional or vector control, and are specifically designed to control the countermovements in treatment. These modules are designed to be used as coordinates with light wire, edge wire, straight wire and twin wire appliances. Also, they may be used singly or in combination.

15 Claims, 23 Drawing Figures

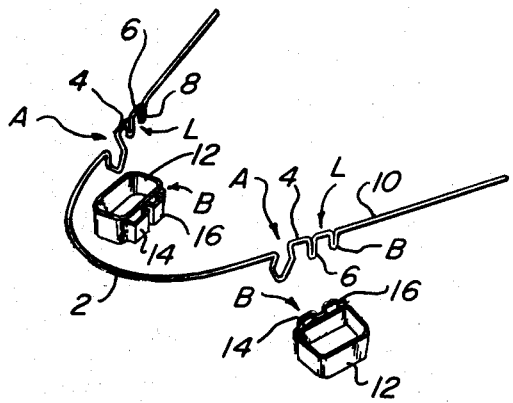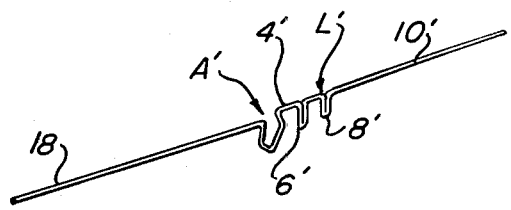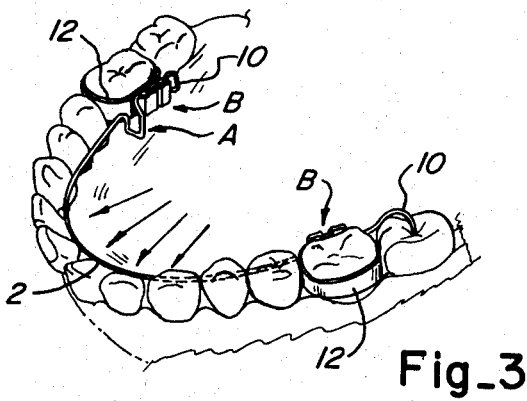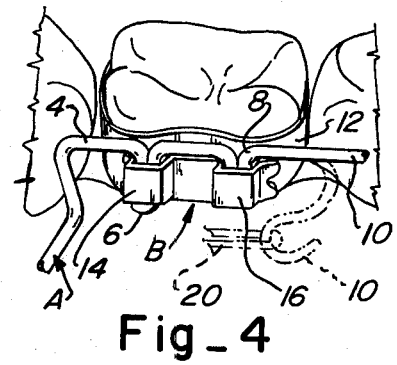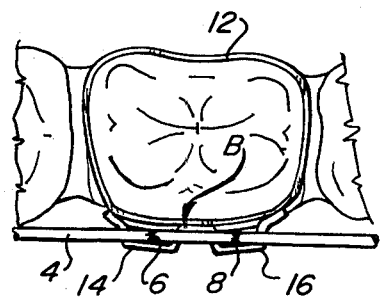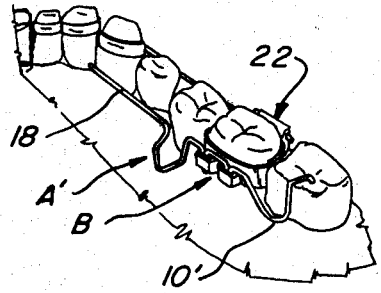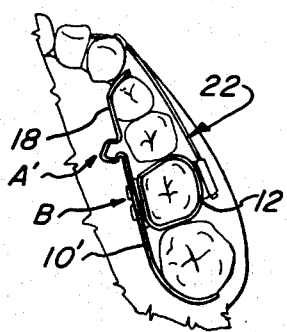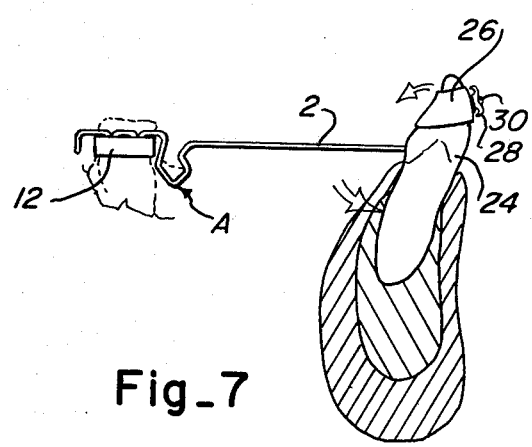

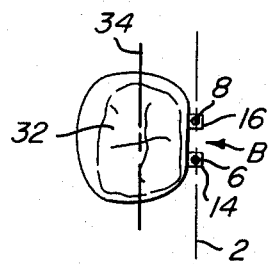
Fig_9
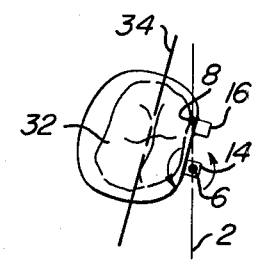
Fig_12
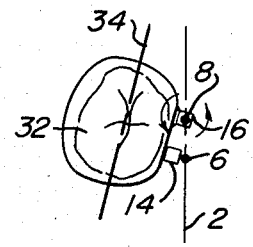
Fig_10
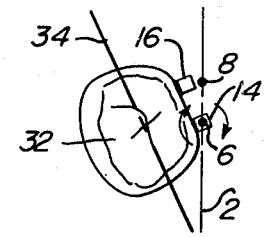
Fig_13
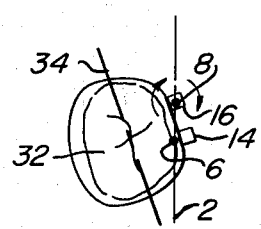
Fig_11

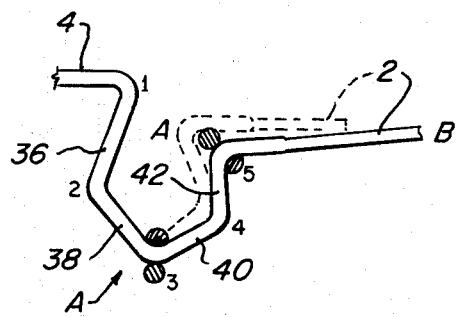
Fig_21
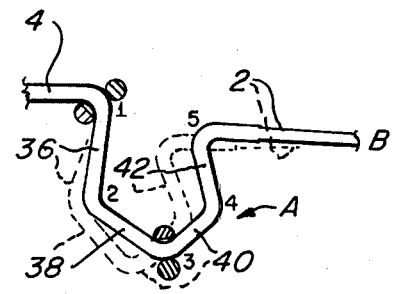
Fig_22
| ADJUSTMENTS | ARCH HEIGHT CHANGE | | ANTERIOR-POSTERIOR INCREMENTS |
|---|---|---|---|
| FIG. 16 | A ↑ | B ↑ | O |
| FIG. 17 | A ↓ | B ↓ | +O |
| FIG. 18 | A O | B ↓ | ++ |
| FIG. 19 | A ↑ | B ↓ | ++ |
| FIG. 20 | A O | B ↑ | O |
| FIG. 21 | A ↓ | B O | ++ |
| FIG. 22 | A ↑ | B O | ++ |
SMALL ARROW INDICATES LESS CHANGE.
LARGE ARROW INDICATES MORE CHANGE.
O INDICATES NO CHANGE.
+ INDICATES SMALL INCREMENTAL CHANGE.
Fig_23

MODULAR ORTHODONTIC APPLIANCES

BACKGROUND OF THE INVENTION

1. Field of the Invention

This invention relates to orthodontic appliances and more particularly to modular orthodontic appliances, the basic modules being an arch wire, a sectional wire and a bracket having twin tubes for receiving twin posts on the wires. These modules have application for treatment of a broad spectrum of orthodontic cases. The modules are designed to be used in cooperation with light wire, edge wire, straight wire and twin wire appliances in any desired combination. Also, a novel activator is used to provide precise directional or vector control.

2. Description of the Prior Art

A large multitude of orthodontic appliances have been used over the years. Most of these have been effective in providing desired tooth movement. However, each separate system was designed around its own parameters and, therefore, one system could not be used with another system and in many cases, with respect to certain types of orthodontic treatment or tooth movement, it was up to the individual orthodontist, through his resourcefulness and experience, to adapt a system with which he was familiar to accomplish the desired result.

As a result, the orthodontist is faced with a problem of stocking a very large number of appliances in order to be able to provide all of the orthodontic needs of his patients. However, because of the considerable cost in stocking a large inventory, the orthodontist will use and stock parts for only that system which he has found most useful or which is within his cost range and that of his patients, but then he may be unable to perform certain orthodontic techniques without ordering special equipment or referring the patient to another orthodontist who has expertise in the use of the particular appliance which is needed. As a result, the cost of orthodontic treatment is increased, the technique used may be inferior to others which are known but which are not readily available to a particular orthodontist, and the time required by the patient to make additional calls to the orthodontist's office and the delays encountered all add up to a situation which is overly costly and frustrating to both the orthodontist and his patient.

Also, the predictability of any directional adjustment of an orthodontic device is subject to the knowledge and skill of the orthodontist and to chance. Thus, undue discomfort can be caused to patients due to misadjustment of orthodontic devices and also unwanted tooth movements and unwanted counter moments are created which are undesirable.

SUMMARY OF THE INVENTION

In accordance with the present invention, a lingual assembly is provided for mounting on the lingual side of teeth of an orthodontic patient. This assembly includes a lingual tube bracket for mounting on a first molar of a patient wherein the bracket includes a first mesial tube and a second distal tube. These tubes are generally parallel to each other and lie along generally vertical axis when mounted on the molar. The lingual assembly also includes a lingual wire for use in the patient's mouth for effecting selective teeth movements. This wire includes a first mesial post receivable in the first mesial tube and a second distal post which is receivable in the second distal tube. The posts are generally parallel to each other and perpendicular to the longitudinal axis of the lingual wire.

In addition, the lingual wire can include a wire segment for engaging the lingual side of the teeth of the patient and an activator connected to the distal end of the wire segment which has a generally polygonal configuration and lies in a plane. The lingual wire also includes an extender segment connected to the distal end of the activator.

More particularly, this invention contemplates either a lingual arch wire or a lingual sectional wire, each of which include a polygonal activator attached to the distal end of the wire. The invention further contemplates a pair of vertical posts attached to the distal end of the activator, the mesial post being longer than the distal post for easy insertion and removal from corresponding tubes in the bracket to provide a tight friction fit when both posts are inserted in the tubes and to provide for torquing the first molar in one direction or the other by bending the lingual wire out of its normal axis so that the posts may be inserted in the bracket whereupon the resiliency of the wire causes it to be activated and apply a resultant force or torque to the tooth. In addition, an extender is attached to the distal end of the distal post which extender may be used for any one of a large variety of orthodontic movements since the extender is not needed to hold the arch wire or sectional onto the bracket on the tooth inasmuch as this is accomplished frictionally by means of the twin post arrangement. Advantageously, the extender may be made to a smaller diameter than the arch wire or segment wire, as by swedging, so that it can be more easily bent for various uses.

Furthermore, in accordance with this invention, a method of orthodontic treatment is provided wherein the vector or directional movement of the lingual assembly is precise and predictable so that the teeth can be moved in a precise and predictable manner. In addition, a method is provided for applying selective torques to the first molar to which the lingual assembly is attached.

Additional advantages of this invention will become apparent from the description which follows, together with the accompanying drawings.

BRIEF DESCRIPTION OF THE DRAWINGS

FIG. 1 is a perspective view of an arch wire and brackets for use therewith forming one embodiment of a modular orthodontic appliance in accordance with this invention;

FIG. 2 is a perspective view of a sectional lingual wire forming a second embodiment of an orthodontic appliance in accordance with this invention;

FIG. 3 is a perspective view of an arch wire of FIG. 1 installed in the mouth of an orthodontic patient for exerting a mesial force on the teeth and showing two uses of the extenders thereon;

FIG. 4 is an enlarged fragmentary perspective view showing the twin posts of a lingual wire inserted in corresponding tubes on a band attached to a molar and showing in dotted lines a further use for an extender;

FIG. 5 is a top plan view of the bracket and twin post construction of the arc wire FIG. 4;

FIG. 6 is a perspective view showing the sectional lingual wire of FIG. 2 installed in the mouth of an orthodontic patient;

FIG. 7 is a horizontal cross section through an arch showing its use with an edge wire for torquing a tooth;

FIG. 8 is a top plan view of a sectional lingual wire showing a further use of the extender thereon;

FIG. 9 is a fragmentary diagrammatic top plan view of a lingual wire having both posts thereof inserted in tubes in a bracket for positive molar control;

FIG. 10 is a top plan view, similar to FIG. 9 but showing the distal post above the distal tube and the axis of the lingual wire intersecting the longitudinal axis of the molar distally thereof prior to insertion of the twin posts into both tubes for mesial-lingual rotation of the molar;

FIG. 11 is a plan view similar to FIGS. 9 and 10 showing the distal post above the distal tube and the axis of the lingual wire intersecting the longitudinal axis of the molar mesially thereof prior to insertion into both tubes to provide mesialbuccal rotation of the molar;

FIG. 12 is a top plan view similar to FIGS. 9-11, but showing the mesial post above the mesial tube and the axis of the lingual wire intersecting the longitudinal axis of the molar distally thereof prior to insertion of the twin posts into both tubes to provide distal-buccal rotation of the molar;

FIG. 13 is a top plan view similar to FIGS. 9-12 but showing the mesial post above the mesial tube and the axis of the lingual wire intersecting the longitudinal axis of the molar mesially thereof prior to insertion of the twin posts into both tubes to provide distallingual rotation of the molar;

FIG. 21 is a view similar to FIGS. 14 and 16-20 showing still a further position of the lingual wire;

FIG. 22 is a view similar to FIGS. 14 and 16-21 showing still another position of the lingual wire; and FIG. 23 is a chart illustrating the adjusted positions of the arch wires as shown in FIGS. 14 and 16-22.

DESCRIPTION OF THE PREFERRED EMBODIMENT

Figure 14:
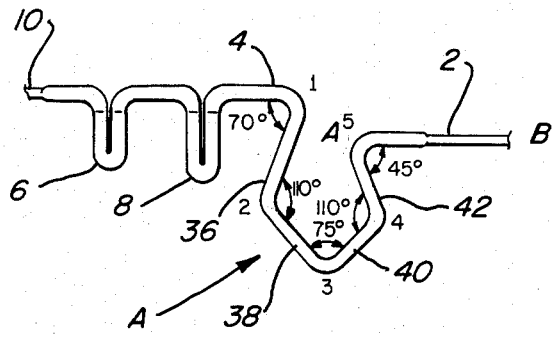
FIG. 14 is an enlarged fragmentary side elevation of a lingual wire showing the standard position thereof.

One form of the invention is shown in FIG. 1 wherein a central arch wire 2 is arcuately formed with integrally formed activators A at the distal ends of the arch wire. Extending distally from the end of each activator is an integral connector wire 4 which in turn integrally connects to a friction lock L having a mesial post 6 and a distal post 8, as shown each of which are generally rectangular in cross section. The lingual assembly terminates in an extender wire 10 also formed integrally at the distal end of friction locks L. Conveniently, the lingual assembly may be installed in the mouth of an orthodontic patient by attaching it to brackets B which are fastened to bands 12 which may be attached to the molars of the patient. Conveniently, a mesial tube 14 and distal tube 16 are formed thereon and each has a generally rectangular opening for receiving the mesial post 6 and distal post 8 as best seen in FIG. 3. The tubes may be formed from a corrugated member as shown and attached to the band, as by welding.

A sectional orthodontic device is shown in FIG. 2 which includes an adapter 18 which is generally straight before installation and has an activator A formed integrally therewith at the distal end which in turn is connected by a small connector wire 4' to a lock L' having a mesial post 6' and a distal post 8' and in turn being formed integrally with an extender 10'.

Although the brackets B are planar when manufactured, they must be bent slightly to conform to the shape of the band to which they are cemented and the shape of the molar on which the band is placed. This slight bending of the bracket then causes the twin post 6 and 8 to fit tightly to form a friction fit with tubes 14 and 16 as best illustrated in FIGS. 4 and 5. It should also be noted that post 6 is slightly longer than post 8 so that it can be guided into tube 14 first followed by post 18 in tube 16 to facilitate easy insertion of the posts in the tubes. This tight friction fit arrangement makes it then possible to use extender 10 for other orthodontic purposes, whereas with a single post connection, it was always necessary to bend the end of the extender 10 around and under the bracket to securely lock the arch wire or segment to the band. For example, extender 10 may be bent as shown in dotted lines in FIG. 4 to provide an anchor for a rubber band 20. In FIG. 3 the extender 10 on the right side of the teeth is shown as a spacer between the first and second molar whereas the extender 10 on the left hand side is used against the second molar to offset counter moments on the first molar. Conveniently, extender 10 is made of smaller diameter, as by swedging, so that it can be bent more easily to the desired shape. FIGS. 6 and 8 show the sectional device of FIG. 2 used for various teeth movements in conjunction with a separate orthodontic appliance 22.

In FIG. 7 illustrates a method of torquing a tooth 24 using a lingual arch in accordance with this invention. As shown, the arch exerts a pressure adjacent the root of the tooth to provide a fulcrum to pivot the tooth in the direction of the arrows. Conveniently, the tooth is provided with a band 26 to which is attached a bracket 28 for receiving an arch wire 30 which applies a posterior pressure to the upper end of the tooth causing this movement.

The lingual arch can be used for molar control and movements as best illustrated diagrammatically in FIGS. 9-13. In FIG. 9, the posts 6 and 8 are each inserted in tubes 14 and 16 in the usual manner as illustrated which provides a neutral non-activated arrangement giving positive molar control for effecting selective tooth movement of other teeth. In FIG. 10 prior to insertion, post 8 lies above tube 16 and because of the misaligned position of molar 32, the longitudinal axis of arch wire 2 is such that it intersects the longitudinal center line 34 of the molar. Insertion of the twin posts into both tubes results in a torque being applied to molar 32 in the direction of the arrows causing a mesial-lingual rotation of molar 32. Similarly, in FIG. 11 prior to insertion, post 8 lies above the tube 16. However, in this situation the molar is misaligned in the opposite direction and, therefore, the torque on the molar is in the opposite direction causing a mesialbuccal rotation upon insertion of the twin posts into both tubes.

In FIG. 12 the front post 6 lies above tube 14 which then applies a torque resulting in the distal-buccal rotation of molar 32 upon insertion of the twin posts into both tubes. As discussed above with respect to FIG. 10, the axis of arch wire 2 is such that it intersects the longitudinal axis 34 of molar 32 because of the displaced position of molar 32.

In FIG. 13 the tooth is displaced in the opposite direction and again post 6 lies above tube 14 which causes a torque to be placed on the tooth to cause a distal-lingual rotation thereof upon insertion of the twin posts into both tubes.

Figure 15:
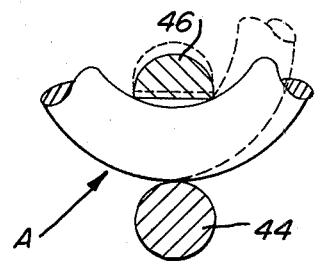
FIG. 15 is a greatly enlarged fragmentary view of one bend in the lingual wire FIG. 14 and showing a pair of pliers applied thereto for increasing the angle of the bend.
Figure 16:
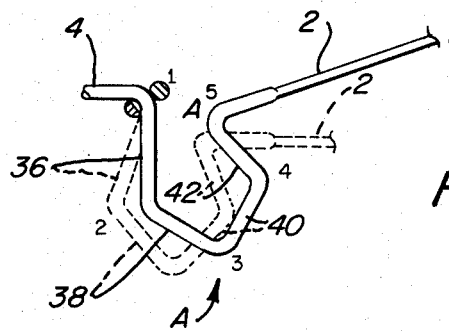
FIG. 16 is a view similar to FIG. 14, but showing a modified position of the lingual wire.

The activator A is shown in detail in FIG. 14 which is the key to providing vectionally predictable incremental movements on selected teeth. The activator is polygonal in shape having a first leg 36 which extends downwardly and distally from connector 4 at an angle of approximately 70° and conveniently is approximately 4 mm. in length. A second leg 38 which is also approximately 4 mm. in length extends downwardly and mesially from first leg 36 at an angle of approximately 110°. A third leg 40 extends upwardly and mesially from second leg 38 at an angle of approximately 75° and is approximately 3 mm. in length. A fourth leg 42 then extends upwardly and distally from third leg 40 at an angle of approximately 110° for a distance of 2 mm. and terminates at arch wire 42 and is connected thereto at an angle of approximately 45%. It has been found that it is the precise angles which permit precise vectional adjustment of the lingual arch wire or lingual segment. Such precise adjustment is not possible with a smooth loop or curve. Of course, it should be understood that the invention contemplates some variation in lengths and distances but that these are considered optimum. To make an adjustment, a pair of pliers is used to change the angle as best seen in FIG. 15. Although various forms of pliers may be used, it has been found that pliers having a pair of conical jaws, one of the jaws being circular in cross section and the other having a flat on the wire engaging surface are the most efficient. Thus, the round concial jaw 44 engages one side of a curve in activator A and the flat jaw 46 engages the other side. As can be seen from the dotted lines, the activator will tend to be bent around the circular jaw 44 when pressure is applied by the flat jaw 46 so as to move from the dotted line position to the solid line position.

Seven different adjustments are shown in FIG. 16–22 and the chart in FIG. 23 shows the movement that is accomplished by each adjustment with respect to arch height change and interior height and posterior movement. Thus, in FIG. 16 by applying the pliers at point 1 as shown, the activator will be bent from the dotted line position to the solid line position causing the posterior end of arch wire 2, i.e., point A to move upwardly slightly and the anterior end of the arch wire 2 at point B to move upwardly substantially. There will be no anterior or posterior change, however.

Figure 17:
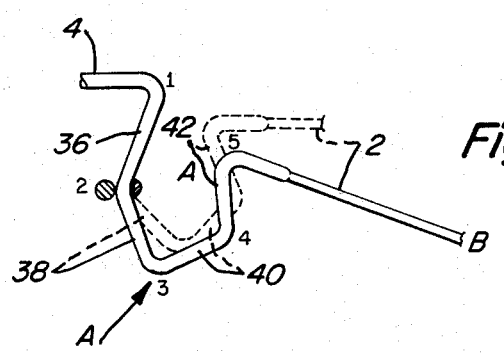
FIG. 17 is a view similar to FIGS. 14 and 16 but showing a still further position of the lingual wire.

In FIG. 17, the pliers are applied at point 2 between legs 36 and 38 causing the activator to move from the dotted line position to the solid line position wherein the posterior end A of arch wire 2 moves downwardly a little bit and the anterior end B moves downwardly substantially. There also will be slight anterior movement of the arch wire.

Figure 18:
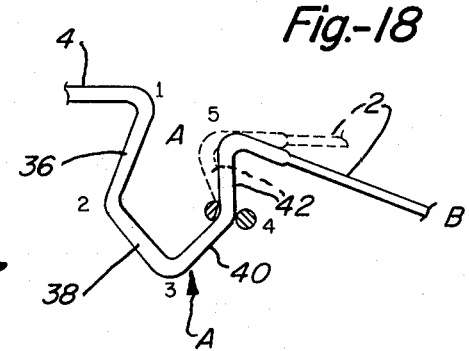
FIG. 18 is a view similar to FIGS. 14, 16 and 17 but showing a further position of the lingual wire.

In FIG. 18 the pliers are applied at point 4 between legs 40 and 42 which moves arch wire 2 from the dotted line position to the solid line position wherein the height of point A thereof stays the same, but point B moves downwardly and there is considerable anterior movement.

Figure 19:
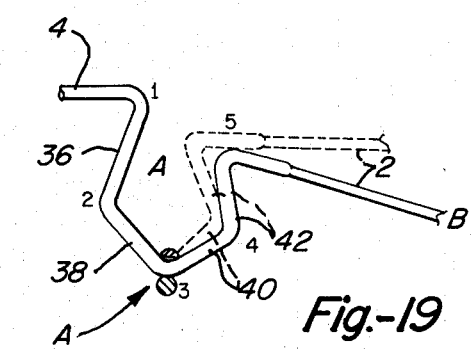
FIG. 19 is a view similar to FIGS. 14 and 16-18 but showing still another position of the lingual wire.

In FIG. 19 plier pressure is applied at point 3 between legs 38 and 40 which causes point A of leg 2 to move downwardly and point B to move downwardly an even greater amount and also results in considerable anterior movement.

Figure 20:
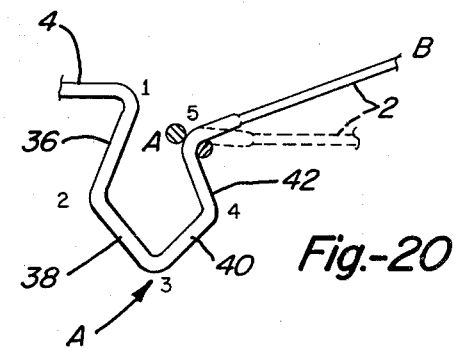
FIG. 20 is a view similar to FIGS. 14 and 16-19 showing a further position of the lingual wire.

In FIG. 20, plier pressure is applied at point 5 between leg 42 and arch wire 2 whereupon point A of arch wire 2 stays the same but point B moves upwardly and there is no anterior-posterior movement.

In FIG. 21, the plier is applied at both points 3 and 5 which results in a downward movement of point A of arch wire 2 but point B stays the same height.

Finally, in FIG. 22, the pliers are applied to both point 1 and point 3 which results in point A moving upwardly, point B staying the same and there is anterior movement of the arch wire 2. Thus, it can be seen that almost any incremental vector change in the position of the arch may be obtained by changing the preset angles in the polygonal activator.

Although the direction of the posts and the activator have been described as extending downwardly, it will be understood that when the orthodontic device of this invention is used on the upper teeth that the directions will be reversed and that the reference to upwardly and downwardly as set forth in the specification and claims is only as a matter of convenience since the specific orientation may be different for particular applications. Furthermore, after installation activator A may be bent about the axis of the wire so that it does not engage the gum of the patient and cause discomfort.

From the foregoing, the advantages of this invention are readily apparent. An orthodontic device has been provided which provides faster tooth movement and less discomfort because of the precise vectorial adjustment which is possible. Further, the modules can be used to coordinate with any other techniques, such as light wire, edge wire, straight wire and twin wire appliances. Also, such use may be made intermediate to or prior to other types of treatment.

In addition, counter movement of molars can be controlled as discussed above and excessive mass root torques can be counteracted by negative forces applied through use of the extender as discussed above. All of this provides better control and precise directional movement by a simple adjustment with pliers.

The twin vertical posts provide a positive lock so that the distal extender may be used for other orthodontic treatment. By having the mesial post longer than the distal post, insertion can be accomplished very rapidly and, of course, removal is equally quick.

Among the lingual arch functions which are possible with this invention are: anchorage; use as a holding arch; interior-posterior increase; buccal expansion; distal molar movement; molar control; molar buccal or lingual torque; molar buccal or lingual tip; molar rotation movements; arch decrease control; leveling; alignment; incisor labial root torque; impacted second molar uprighting; use with a transpalatal bar; use with a 6—6 retainer; use with a Nance holding arch; use with habit breakers; use with space maintainers; and variable tooth movement with finger springs. Variable functions that are possible with the sectional lingual device are: use as mesial elastic hook; use as a cross elastic hook; use as a second molar depresser; use as a second molar uprighter; use as an impacted second molar distalizer; use as a first bicuspid retractor; use as a second bicuspid space opener; use as a second biscuspid buccal uprighter; use as a bicuspid depressor; use as a bicuspid rotator; use as a simple expander; use as a stationary expander; use as a posterior anchorage; use as a cantalever resistor; use for impacted cuspid control; and for many other individualized applications.

The invention has been described in detail with particular reference to preferred embodiments thereof, but it will be understood that variations and modifications can be effected within the spirit and scope of the invention.

What is claimed is:

1. A lingual assembly for mounting on the lingual side of the teeth of an orthondontic patient, said assembly comprising:
   a lingual tube bracket for mounting on a first molar of the patient, said bracket including:
   a first mesial tube having a generally rectangular opening; and
   a second distal tube having a generally rectangular opening, said tubes being generally parallel to each other and lying along generally vertical axes when mounted on the molar; and
   a lingual wire, having a longitudinal axis for use in the patient's mouth for effecting selective teeth movements, said wire including:
   a first mesial post having a generally rectangular cross section receivable in said first mesial tube;
   a second distal post having a generally rectangular cross section receivable in said second distal tube, said posts being generally parallel to each other and lying in the same plane and perpendicular to the longitudinal axis of said lingual wire;
   an extender segment extending distally from said distal post which is bendable for use in tooth movement;
   a connector segment extending mesially from said mesial post;
   and adjustable activator extending mesially from said connector segment for accomplishing any one of a large variety of orthodontic movements, said activator generally lying in the plane of said posts and, including:
   a first leg extending downwardly and distally from said connector segment;
   a second leg extending downwardly and mesially from said first leg;
   a third leg extending upwardly and mesially from said second leg;
   a fourth leg extending upwardly and distally from said third leg; and
   a wire segment extending mesially from the upper end of said fourth leg.

2. A lingual assembly as claimed in claim 1 wherein:
said first and second legs are substantially the same length;
said third leg is approximately three-fourths the length of said first and second legs; and
said fourth leg is approximately one-half the length of said first and second legs.

3. A lingual assembly as claimed in claim 1 wherein:
said first leg is connected to said connector segment at a first acute angle;
said second leg is connected to said first leg at a first obtuse angle;
said third leg is connected to said second leg at a second acute angle;
said fourth leg is connected to said third leg at a second obtuse angle; and
said fourth leg is connected to said wire segment at a third acute angle.

4. A lingual assembly as claimed in claim 3 wherein:
said obtuse angles are substantially equal.

5. A lingual assembly as claimed in claim 1 wherein:
said wire segment is substantially straight before use.

6. A lingual assembly as claimed in claim 1 wherein:
said wire segment is in the form of an arch and has a corresponding activator and extender segment on the other end thereof.

7. A lingual wire for use in the mouth of an orthodontic patient for effecting selective teeth movements, said lingual wire including:
   a wire segment for engaging the lingual side of the teeth of the patient;
   an extender segment;
   an adjustable activator interconnecting said wire segment and said extender segment for accomplishing any one of a large variety of orthodontic movements including:
   a first leg extending downwardly and distally from said extender segment;
   a second leg extending downwardly and mesially from said first leg;
   a third leg extending upwardly and mesially from said second leg; and
   a fourth leg extending upwardly and distally from said third leg, said wire segment being connected to the upper end of said fourth leg.

8. A lingual wire as claimed in claim 7 wherein:
said first and second legs are substantially the same length;
said third leg is approximately three-fourths the length of said first and second legs; and
said fourth leg is approximately one-half the length of said first and second legs.

9. A lingual wire as claimed in claim 8 wherein:
said first and second legs are approximately 4 mm. in length;
said third leg is approximately 3 mm. in length; and
said fourth leg is approximately 2 mm. in length.

10. A lingual wire as claimed in claim 8 wherein:
said first leg is connected to said extender segment at first acute angle;
said second leg is connected to said first leg at a first obtuse angle;
said third leg is connected to said second leg at a second acute angle;
said fourth leg is connected to said third leg at a second obtuse angle; and
said fourth leg is connected to said wire segment at a third acute angle.

11. A lingual wire as claimed in claim 10 wherein:
said obtuse angles are substantially equal.

12. A lingual wire as claimed in claim 10 wherein:
said first acute angle is approximately 70°; said obtuse angles are each approximately 110°; said second acute angle is approximately 75°; and said third acute angle is approximately 45°.

13. A lingual wire for use in the mouth of an orthodontic patient for effecting teeth movements, said lingual wire including:
   a mesial wire segment for engaging the lingual side of the teeth of the patient;

a distal extender segment; and an activator interconnecting said mesial wire segment and said distal extender segment, said activator being polygonal and lying in a plane and including:

a first leg extending downwardly and distally from said extender segment at an angle of 70° and for a distance of 4 mm.;

a second leg extending downwardly and mesially from said first leg at an angle of 110° and for a distance of 4 mm.;

a third leg extending upwardly and mesially from said second leg at an angle of 75° and for a distance of 3 mm.; and a fourth leg extending upwardly and distally from said third leg at an angle of 110° and for a distance of 2 mm. and being connected at its upper end to said wire segment.

14. A lingual wire as claimed in claim 13 wherein: said wire segment is substantially straight before use.

15. A lingual wire as claimed in claim 13 wherein: said wire segment is in the form of an arch and has a corresponding activator and extender segment on the other end thereof.

* * * * *